March 5, 1968 C. PREUSS Plant Pat. 2,797
PEACH TREE
Filed Nov. 21, 1966
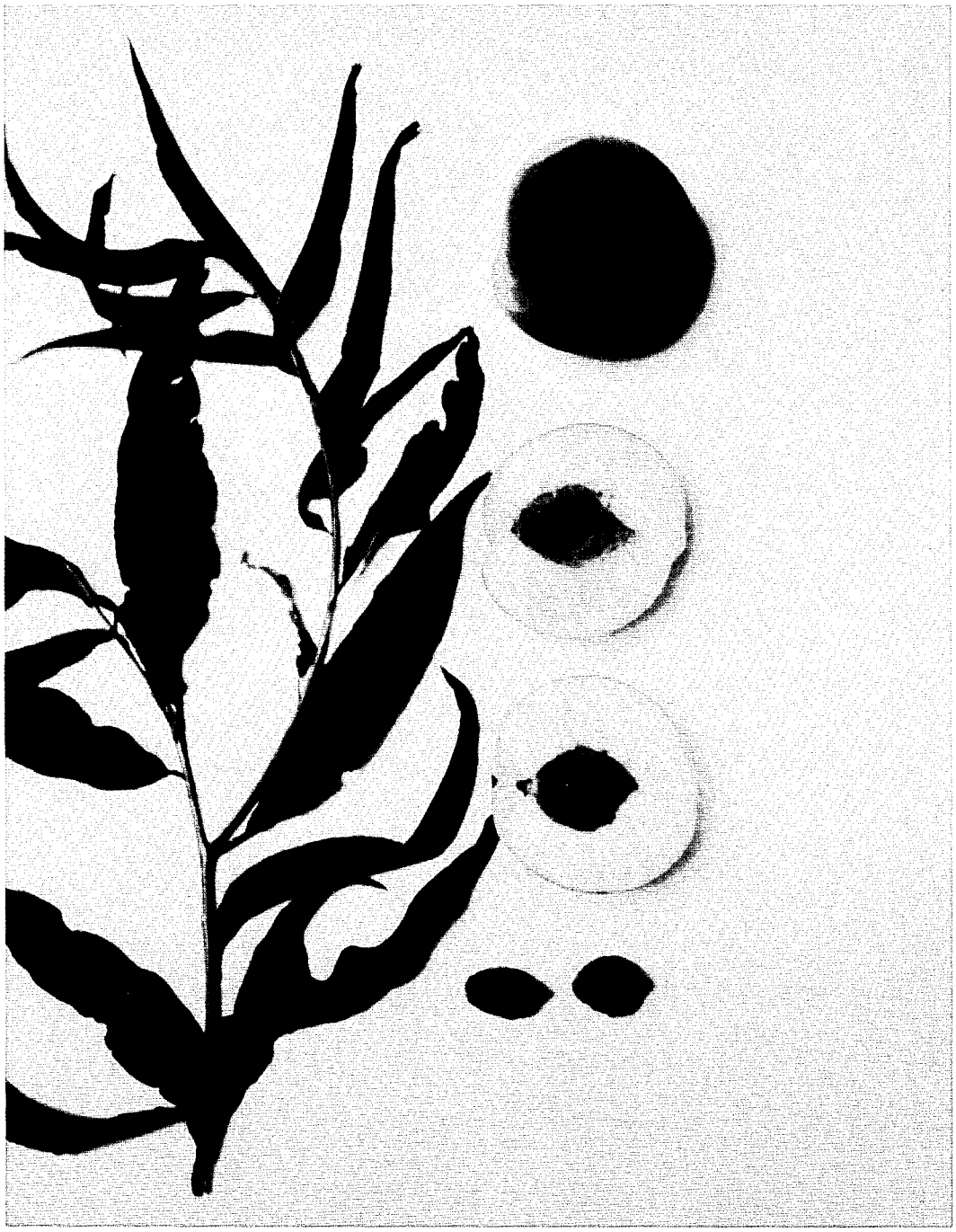
CHARLES PREUSS
INVENTOR
Huebner & Worrel
ATTORNEYS United States Patent Office Plant Pat. 2,797
Patented Mar. 5, 1968

2,797
PEACH TREE
Charles Preuss, 8690 N. Minnewawa,
Clovis, Calif. 93612
Filed Nov. 21, 1966, Ser. No. 596,022
1 Claim. (Cl. Plt.—43)

The present invention relates to a peach tree and more particularly to a new and distinct variety thereof broadly characterized by its vigorous growth and large size; regular and heavy bearing; and the production of relatively large free-stone, darkly red-skinned, firmly textured, yellow-fleshed peaches.

The instant variety peach tree blooms during the latter part of March at about the same time as the Fay Elberta (unpatented) peach tree. Its fruit ripens during the latter part of July, usually approximately midway between the ripening of the fruit of the Suncrest (unpatented) peach tree and the fruit of the Fay Elberta (unpatented) peach tree. Such ripening occurs at about the same time as the ripening of the fruit of the Merrill 49er (unpatented) peach tree. The fruit of the instant variety, however, distinguishes from the fruit of the Merrill 49er in being more uniformly round, having a redder skin color, and a smoother suture which in the Merrill 49er is frequently open to the stone. The fruit of the instant variety most nearly resembles the fruit of its parent Suncrest (unpatented) peach tree but distinguishes therefrom in its ripening approximately ten days later, in its more darkly colred red suture, and in its sweeter flavor.

My new variety of peach tree was discovered by me in July 1962 as a sport growing on a Suncrest (unpatented) peach tree in my orchard at 8690 North Minnewawa Avenue, Clovis, Fresno County, Calif. Buds from the sport were budded by me at my above designated orchard into a number of Nemaguard peach tree rootstocks and into a number of seedling Redglobe peach trees in the spring of 1963. In the spring of 1964, buds from these trees were budded into a five-acre plot of Nemaguard peach tree rootstocks in the same orchard. The resulting trees fruited in July of 1966 and the fruit and tree characteristics resulting from such budding proved identical to those of the original sport. It is significant to note that these trees produced approximately one-hundred lug boxes of peaches (about 2500 lbs.) in their first full bearing year.

The accompanying drawing is a color photograph of two mature fruit of the subject variety with one divided on its suture plane to reveal flesh coloration and pit characteristics together with two additional stones and a representative twig showing the leaves.

Referring more specifically to the pomological details of this new and distinct variety of peach tree, the following has been observed under the ecological conditions prevailing at the orchard at Clovis, Fresno County, Calif., and is an outlined description thereof. All major color plate identifications are by reference to the Nickerson Color Fan of the American Horticultural Council.

*Tree*

Size: Large vigorous, with shape and density determined by pruning methods.
Trunk: Medium stocky, medium smooth.
Branches: Lenticels, numerous, medium sized.
Leaves: Medium large.
- *Length.*—Average 6".
- *Width.*—Average 1½".
- *Form.*—Lanceolate, tip acuminate.
- *Color.*—Upper surface, dark greyish-green (10GY 3/2); under surface, dark yellowish-green (2.5G 3/3).
- *Class* (Meader & Blake: Proceedings of Am. Soc. Hor. Sc., vol. 37, page 206).—1, 2 and 3.
- *Margin.*—Crenate, averaging nine serrations per inch.
- *Petiole.*—Medium long, average ⅜", medium slender, average ⅛" in diameter.
- *Glands.*—Varying in number from five to six on petiole and base of leaves, reniform.
- *Stipules.*—Usually two in opposed relation.

Flower buds: Generally large, plump, free, pubescent.
Flowers: Large size, self-fertilizing, bloom at about the same time as the Fay Elberta (unpatented) peach tree, mostly light pink, some darkening to light red.

*Fruit*

Maturity when described, firm ripe.
Size: Large.
- *Axial diameter.*—2½" to 2¾", average 2⅝", under normal environmental and horticultural conditions with usual thinning to space fruit on fruit-bearing branches.
- *Transverse in suture plane.*—2¾" to 3¼", average 3".
- *At right angle to suture plane.*—2⅞" to 3⅛", average 3".

Form: Generally globose, symmetrical to asymmetrical.
- *Suture.*—Well filled, distinctive dark red line from stem to pistil point with slight depression adjacent to the pistil point.
- *Ventral surface.*—Rounded, lips equal.
- *Cavity.*—Abrupt, deep.
- *Depth.*—Average ½".
- *Breadth.*—Average ¾".
- *Base.*—Retuse.
- *Apex.*—Generally flat, small tip.
- *Pistil point.*—Small, apical.
- *Stem.*—Length, ⅜" to ½", average 7/16". Diameter—average ⅛".

Skin: Medium thin.
- *Under color.*—Yellow (2.5Y 8/12) with varying amounts of dark red (2.5R 3/7) covering approximately 80% of the surface.
- *Down.*—Scant, short, fine-textured, minimum cracking tendency.

Flesh:
- *Color.*—Yellow (5Y 8/12) with some red flecking near the pit.
- *Amygdalin.*—Moderate.
- *Juice.*—Abundant.
- *Flavor.*—Sweet, less tart than the fruit of the parent Suncrest peach tree.
- *Aroma.*—Distinct.
- *Texture.*—Generally firm.
- *Fibers.*—Medium.
- *Ripens.*—Uniformly.
- *Eating quality.*—Excellent.

Stone: Generally free from the flesh.
- *Fibers.*—Short.
- *Size.*—Length, average 1¼". Breadth, average ⅞". Thickness, average ⅝".
- *Form.*—Generally obovate, tip acuminate and transversely offset from longitudinal axis.
- *Base.*—Straight.
- *Sides.*—Unequal; one side convex, opposite side concave adjacent to the tip.
- *Surface.*—Irregulary furrowed, pitted toward tip.
- *Ridges.*—Medium.
- *Color.*—Reddish brown.
- *Splitting tendency.*—Virtually none.

Use: Fresh market, local and distant, culinary.
- *Keeping quality.*—Excellent.
- *Shipping quality.*—Excellent.

Although the new variety of peach tree possesses the described characteristics of the growing conditions in Fresno County, Calif., in the central portion of the San Joaquin Valley, it is to be understood that variation of the usual magnitude in characteristics incident to growing conditions, fertilization, pruning and pest control are to be expected.

Having thus described and illustrated my new variety of peach tree, what is claimed as new and desired to be secured by Letters Patent is:

1. A new and distinct variety of peach tree substantially as illustrated and described and which is characterized by its vigorous growth and its regular and heavy bearing of freestone, darkly red skinned, firm textured, yellow-fleshed peaches which ripen about ten days earlier than the fruit of the Fay Elberta (unpatented) peach tree, about ten days later than the fruit of its parent Suncrest (unpatented) peach tree, and at about the same time as the fruit of the Merrill 49er (unpatented) peach tree from which varieties of peach trees the instant variety distinguishes in its relatively larger, generally more uniformly round fruit having a smoother distinctive darkly red lined suture with its skin being more darkly red colored and distributed over a larger portion of the skin and which contains a stone having a pointed tip transversely offset from its longitudinal axis.

No references cited.

ROBERT E. BAGWILL, *Primary Examiner.*